United States Patent [19]

Beelman et al.

[11] Patent Number: 5,681,738

[45] Date of Patent: Oct. 28, 1997

[54] USE OF 10-OXO-TRANS-8-DECENOIC ACID IN MUSHROOM CULTIVATION

[75] Inventors: Robert B. Beelman; Gregory R. Ziegler; Jeng-Leun Mau, all of State College, Pa.

[73] Assignee: The Penn State Research Foundation, University Park, Pa.

[21] Appl. No.: 854,114

[22] Filed: Mar. 19, 1992

[51] Int. Cl.$^6$ .................. A01G 1/04; C05F 11/02; C12N 5/00; C12N 5/02

[52] U.S. Cl. .................. 435/254.1; 47/1.1; 71/5; 71/24; 71/901; 71/904; 435/240.4; 504/201; 504/321

[58] Field of Search .................. 435/240.4, 254.1; 71/5, 24, 63, 901, 904; 47/1.1; 504/201, 321

[56] References Cited

U.S. PATENT DOCUMENTS

| | | | |
|---|---|---|---|
| 4,127,964 | 12/1978 | Mee | 47/1.1 |
| 4,127,965 | 12/1978 | Mee | 47/1.1 |
| 4,333,757 | 6/1982 | Kurtzman, Jr. | 71/5 |
| 4,848,026 | 7/1989 | Dunn-Coleman et al. | 47/1.1 |
| 5,186,731 | 2/1993 | Parker | 71/5 |

FOREIGN PATENT DOCUMENTS

| 9116281 | 10/1991 | WIPO | 47/1.1 |
|---|---|---|---|

OTHER PUBLICATIONS

Tressl et al (1982) *J. Agric. Food Chem.* 30:89–93.

Hagimoto et al (1959) *Bot. Mag. Tokyo*, 72(855)359–66.

Zimmerman et al (1979) *Plant Physiol.* 63:536–41.

Wurzenberger et al (1982) *Z Lebensm Unters Forsch* 175:186–190.

Hagimoto et al (1960) *Bot. Mag. Tokyo* 73:283–287.

Royse et al (1980) *Interdisciplinary Science Reviews* 5(4):324–31.

*Primary Examiner*—Douglas W. Robinson
*Assistant Examiner*—Deborah K. Ware
*Attorney, Agent, or Firm*—Thomas J. Monahan

[57] ABSTRACT

Provided is a method for the use of 10-oxo-trans-8-decenoic acid (ODA) as a fungal growth hormone to stimulate mycelial growth of cultivated mushrooms. A species of cultivated mushroom is selected and grown in a solid or liquid growth medium which has been supplemented with ODA to a concentration of $10^{-7}$M to about $10^{-4}$M. After culturing the mushroom the mycelium of cultivated mushroom is harvested. In addition to a method of using ODA, a method for the hormonal stimulation of fruiting in cultivated mushrooms is also disclosed. The ODA in this method is added to the casing layer of the compost which is mixed with mushroom spawn. Further, the ODA is added to the casing layer in aqueous solution after casing the compost.

4 Claims, 12 Drawing Sheets

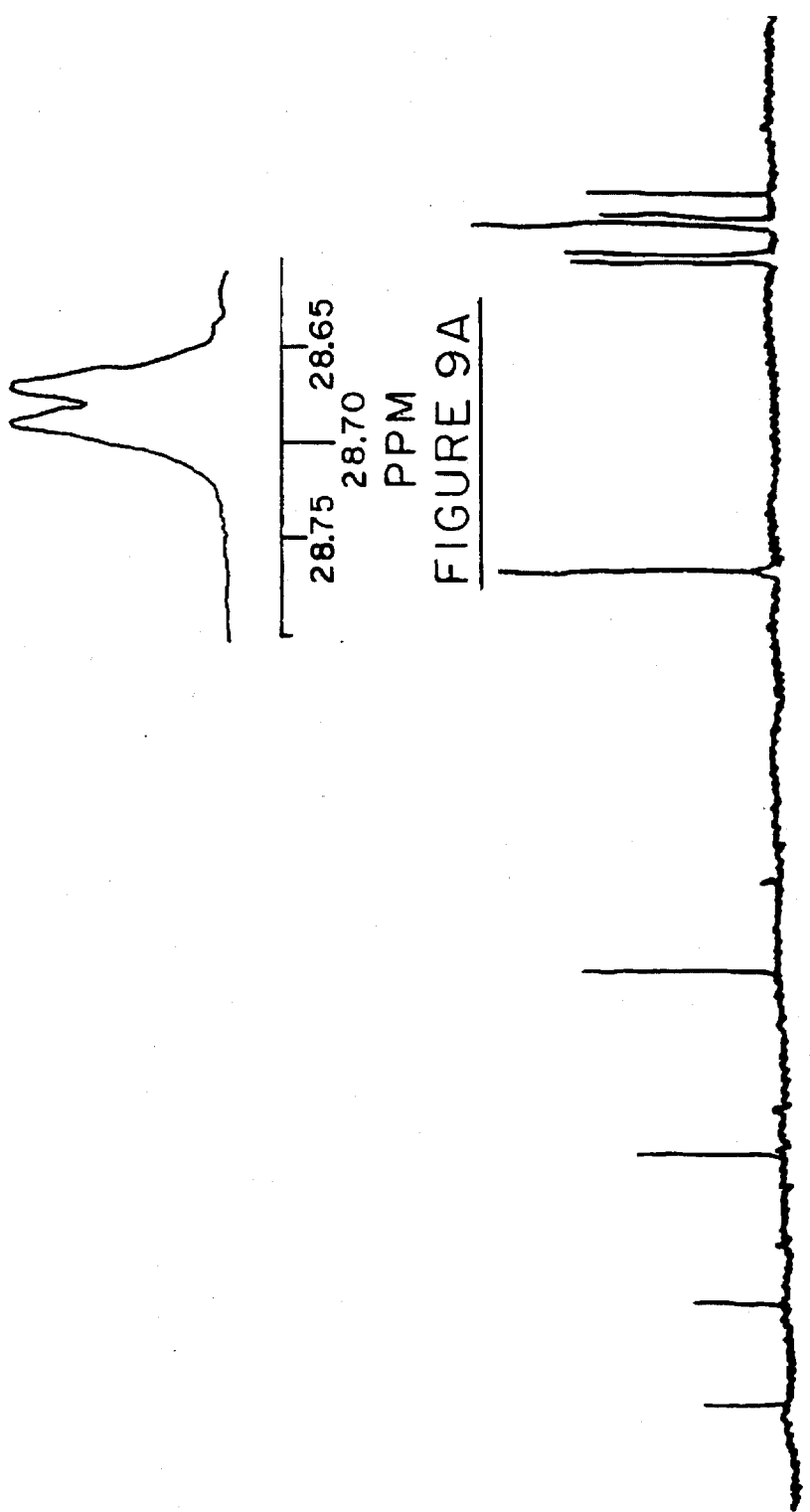
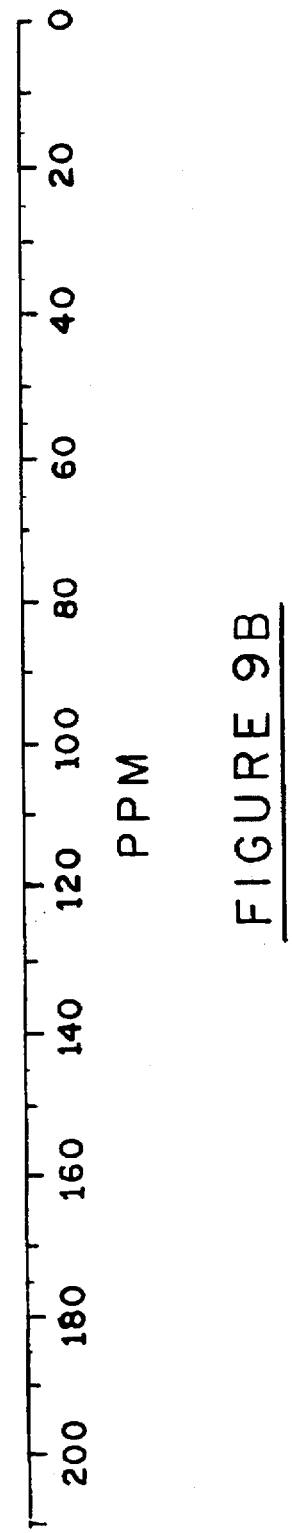
FIGURE 9A
FIGURE 9B

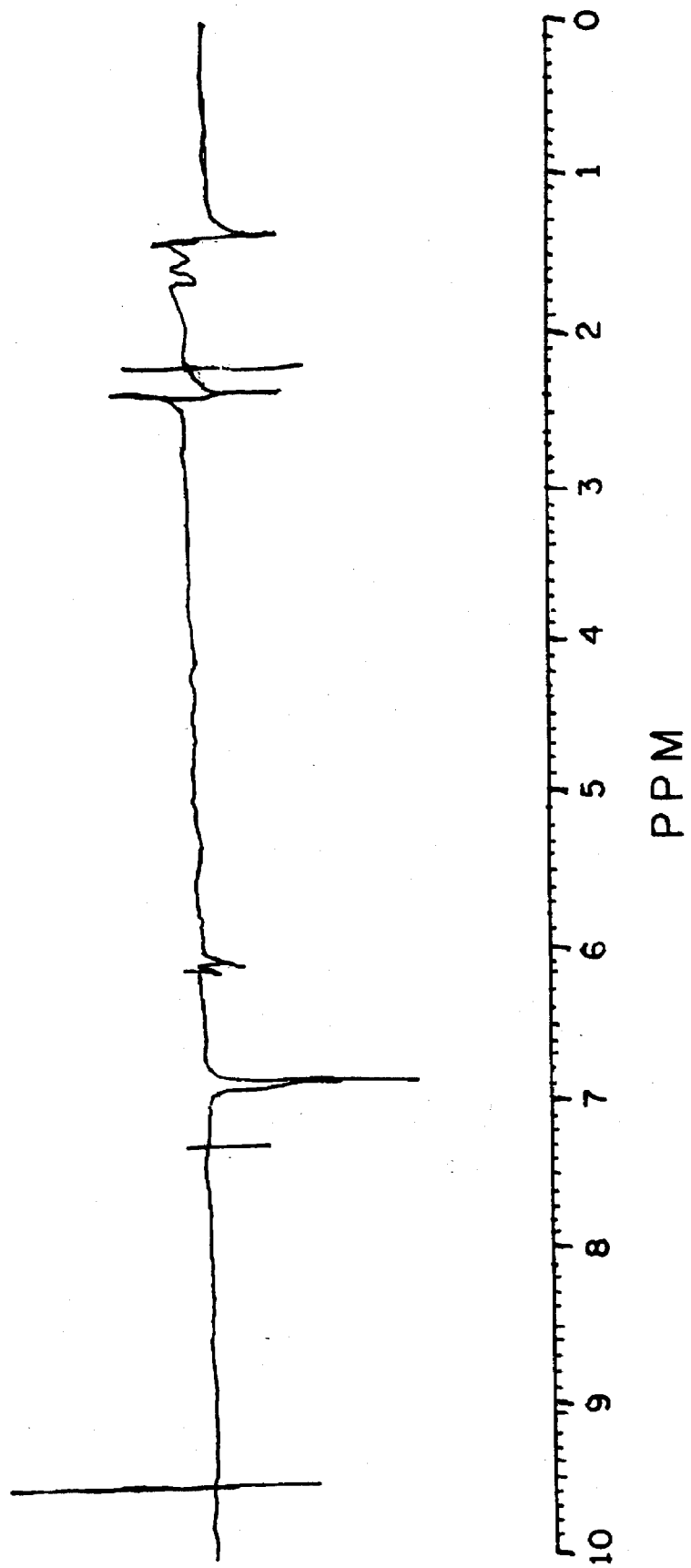

Flow diagram for preparation and test of a separated mushroom stipe.

USE OF 10-OXO-TRANS-8-DECENOIC ACID IN MUSHROOM CULTIVATION

BACKGROUND OF THE INVENTION

1. Field of the Invention

The present invention relates to the isolation and purification of 10-oxo-trans-8-decenoic acid, ODA, from natural sources, and the use thereof to stimulate fungal growth in cultivation and fermentation processes.

2. Description of Related Art

Many higher plant hormones have been found in the mushroom, including indole-3-acetic acid, auxins, gibberellins, ethylene, cytokinins and zeatins (Hammond et al., (1985)). However, none of these has proven to have a hormonal effect on mushrooms. Several investigators have found evidence for a factor mainly produced in the gills promoting stipe elongation (Hagimoto et al., (1959), Hagimoto et al., (1960), Gruen (1963), Gruen (1967), Gruen (1982)), but, to date, this factor has not been identified.

10-Oxo-trans-8-decenoic acid (ODA) produced in Agaricus mushrooms was first reported by Tressl et al., (1982) as one of the enzymatic breakdown products of linoleic acid. Later, this compound was isolated as its corresponding methyl ester when Wurzenberger et al., (1982) studied the biosynthetic formation of 1-octen-3-ol in common mushrooms. An enzymatic pathway was then proposed for the breakdown of linoleic acid to form 1-octen-3-ol and 10-oxo-trans-8-decenoic acid via lipoxygenase (linoleate:oxygen oxidoreductase, EC 1.13.11.12) and hydroperoxide lyase (no systematic name and code number available) (Grosch et al., 1984). Lipoxygenase and hydroperoxide lyase in mushrooms are rather different compared to those in higher plants, inasmuch as they are very specific for incorporating oxygen into linoleic acid at the C-10 position and unconjugating the 10-hydroperoxide of linoleic acid to form 1-octen-3-ol and ODA (Wurzenberger et al., 1984a,b).

1-Octen-3-ol, also known as mushroom alcohol, contributes significantly to the characteristic flavor of mushrooms because of its intense mushroom-like aroma and extremely low sensory threshold value (Cronin et al., 1971; Dijkstra el al., 1976; Pyysalo et al., 1976; Fischer et al., 1987). Thus, 1-octen-3-ol is produced in the Basidiomycetes and other edible fungi, and serves as an important "sensorial principle," but some C10-compounds, including ODA, might be "very potent aromatics, pheromones, and wound hormones" (Tressl et al., 1981).

The compound, 9-oxo-cis-2-decenoic acid, which has the same chemical formula and functional groups as ODA, is known as "queen substance", and is the sex pheromone of honey bees (Butler et al., 1959). In higher plants, C6-compounds with "green note" and 12-oxo-trans-10-dodecenoic acid are formed from the breakdown of linoleic acid by lipoxygenase and hydroperoxide lyase. 12-Oxo-trans-10-dodecenoic acid was characterized as the wound hormone, traumatin (Zimmerman et al., 1979). It was found to induce the formation of an intumescence on the seed chamber of runner bean (Zimmerman et al., 1979).

Tressl et al., (1982) identified several C10-compounds, including ODA, produced in mushrooms. Wurzenberger et al., (1982, 1984a,b,c) methylated ODA into its corresponding methyl ester for further isolation and identification. However, no attempt was made to isolate and purify ODA in its acid form.

The cultivation of common button mushrooms (Agaricus bisporus) is of great economic importance, and involves several different production stages including composting, spawning, casing, CACing and picking. (Gaze, (1985)). At spawning, pasteurized compost is innoculated with mushroom spawn, a mixture of mushroom mycelia and grain colonized by such mycelia, used to "seed" mushroom compost. Two to three weeks are required for the mycelia to colonize the compost. After mycelial colonization, the compost is covered with a casing layer, comprising a layer of soil, or a mixture of soil and sphagnum peat with chalk added, or peat moss with chalk added, or any of the foregoing mixed with CACing material, i.e., colonized compost, to induce fruiting. Fruiting occurs 2 weeks after casing and following severe manipulation of environmental conditions (lower temperature and reduced $CO_2$ concentration) (Flegg et al., (1985)). The most limiting factor in the cultivation of a mushroom crop is the time required for the colonization of the compost and subsequently the casing layer by the mycelium and the initiation of fruiting bodies. Despite numerous studies, the factors which promote mycelial growth and initiate fruiting are still not well understood. Reduction of the growth period following spawning and casing would improve the economics of mushroom cultivation, and the identification of growth and fruiting simulator(s) or hormone(s) would contribute toward this goal.

SUMMARY OF THE INVENTION

The present inventors have isolated a compound from mushrooms and identified it as 10-oxo-trans-8-decenoic acid (ODA) (Mau, 1992). This compound is produced concurrently with the major mushroom aroma component, 1-octen-3-ol, especially when tissues of fruiting bodies or filaments of the mycelium are damaged or disrupted (Grosch et al., (1984), Schindler (1989)). 1-Octen-3-ol has been found in other fungi, such as Aspergillus and Penicillium spp. (Kaminski et al., (1974)). Thus, by inference, it can be assumed that ODA is also concurrently produced. ODA produced in Agaricus mushrooms was first reported as an enzymatic breakdown product of linoleic acid (Tressl et al., (1982)). Later, this compound was isolated as its corresponding methyl ester when the biosynthetic formation of 1-octen-3-ol in mushrooms was established (Wurzenberger et al., (1982)). ODA has a structure similar to "queen substance" (9-oxo-cis-2-decenoic acid, the sex pheromone of honey bees) (Butler et al., (1959)) and traumatin (12-oxo-trans-10-dodecenoic acid, a wound hormone in higher plants) (Zimmerman et al., (1979)). As a homologue, ODA might be expected to have similar physiological effects on mushrooms or fungi.

The research reported herein was undertaken to isolate and characterize ODA from mushrooms, and to elucidate the physiological effects of ODA on mushrooms and other fungi by examining its influences on the growth of mushroom mycelia and the elongation of mushroom stipes. The effect of ODA, in the form of mushroom powder, on a mushroom crop was also studied, as was the effect of ODA on the fermentation of other fungi.

Accordingly, it is an object of the present invention to provide a method of isolating 10-oxo-trans-8-decenoic acid, ODA, comprising the steps of:

(a) homogenizing mushrooms in a buffer containing linoleic acid to produce a homogenate;

(b) extracting said homogenate with an organic solvent in which said ODA is soluble to produce an ODA-containing extract;

(c) chromatographing said ODA extract through an adsorbent medium; and

3

(d) recovering purified ODA.

Another object of the present invention is to provide purified, isolated ODA of formula I:

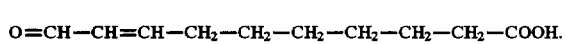
(I)

in the form of a free acid.

Another object of the present invention is to provide a method for initiating fruiting and increasing yield in mushroom cultivation, comprising adding 10-oxo-trans-8-decenoic acid, ODA, a derivative thereof exhibiting at least one ODA effect, or a combination of two or more of said ODA or derivatives thereof exhibiting at least one ODA effect, during mushroom cropping.

It is another object of the present invention to provide a CACing material for use in mushroom cultivation comprising spawn-run compost or other suitable material inoculated with viable mycelium containing 10-oxo-trans-decenoic acid, ODA, a derivative thereof exhibiting at least one ODA effect, or a combination of two or more of said ODA or derivatives thereof exhibiting at least one ODA effect.

A further object of the present invention is to provide a composition for stimulating fungal growth, comprising:

- a fungal yield enhancing effective amount of 10-oxo-trans-8-decenoic acid, ODA, a derivative thereof exhibiting at least one ODA effect, or a combination of two or more of said ODA or derivatives thereof exhibiting at least one ODA effect; and
- a fungally acceptable carrier.

A further object of the present invention is to provide a method for producing mushroom spawn, comprising adding 10-oxo-trans-8-decenoic acid, ODA, a derivative thereof exhibiting at least one ODA effect, or a combination of two or more of said ODA or derivatives thereof exhibiting at least one ODA effect to sterilized grain or a liquid culture inoculated with mycelia for the purpose of producing spawn.

A further object of the present invention is to provide a synthetic delivery system for delivering 10-oxo-trans-8-decenoic acid, ODA, a derivative thereof exhibiting at least one ODA effect, or a combination of two or more of said ODA or derivatives thereof exhibiting at least one ODA effect, comprising said ODA, said derivative or said combination encapsulated in an encapsulating material.

A further object of the present invention is to provide a method for stimulating mycelial growth in a fungus, comprising contacting mycelia of said fungus with 10-oxo-trans-8-decenoic acid, ODA.

A still further object of the present invention is to provide a method for stimulating mycelial growth in a fungus, comprising contacting mycelia of said fungus with at least one of 10-oxo-trans-8-decenoic acid, ODA, a derivative of ODA exhibiting at least one ODA effect, or a combination of two or more of said ODA or ODA derivatives exhibiting at least one ODA effect.

Further scope of the applicability of the present invention will become apparent from the detailed description and drawings provided below. However, it should be understood that the detailed description and specific examples, while indicating preferred embodiments of the invention are given by way of illustration only since various changes and modifications within the spirit and scope of the invention will become apparent to those skilled in the art from this detailed description.

BRIEF DESCRIPTION OF THE DRAWINGS

The above and other objects, features, and advantages of the present invention will be better understood from the following detailed descriptions taken in conjunction with the accompanying drawings, all of which are given by way of illustration only and are not limitative of the present invention, which depict the following:

FIG. 9. $^{13}$C-Nuclear magnetic resonance spectrum of 10-oxo-trans-8-decenoic acid in $CDCl_3$ with an enlargement region of an overlapping peak at 28.65–28.75 ppm.

FIG. 10. $^1$H-Nuclear magnetic resonance spectrum of 10-oxo-trans-8-decenoic acid in $CDCl_3$ with an irradiation of H at C9.

DETAILED DESCRIPTION OF THE INVENTION

The contents of each of the references cited in the present application are herein incorporated by reference in their entirety.

The following detailed description of the invention is provided to aid those skilled in the art in practicing the present invention. Even so, the following detailed description should not be construed to unduly limit the present invention, as modifications and variations in the embodiments herein discussed may be made by those of ordinary skill in the art without departing from the spirit or scope of the present inventive discovery.

EXAMPLE 1

Figure 1:
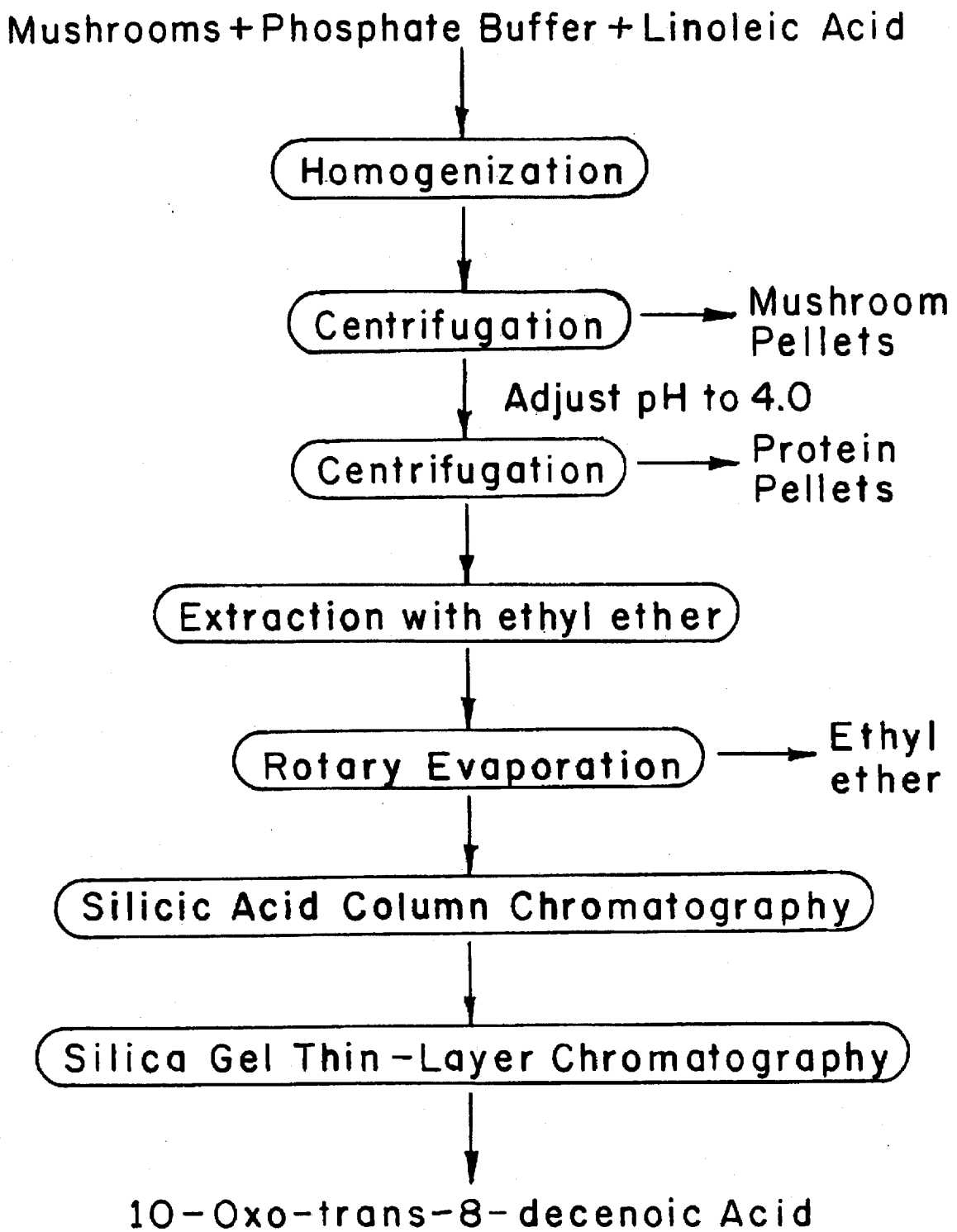
FIG. 1. Flow diagram for preparation and purification of 10-oxo-trans-8-decenoic acid.

Isolation and identification of the 10-Oxo-trans-8-decenoic Acid from Agaricus bisporus Mushroom material The cultivated common mushroom, a hybrid off-white strain of Agaricus bisporus (Lange) Imbach, was obtained from the Mushroom Test and Demonstration Facility (MTDF) on The Pennsylvania State University campus. The preparation and purification of 10-oxo-trans-8-decenoic acid (ODA) is summarized in FIG. 1.

Preparation and Isolation of 10-Oxo-trans-8-decenoic Acid

Mushrooms (400 g) were cut into small cubes and homogenized with 400 mL of 0.1M sodium phosphate buffer (pH 6.5) containing 0.10% Tween 80 and 500 mg linoleic acid (Aldrich Chemical Co., Milwaukee, Wis.) for 2 min. The mushroom homogenate was centrifuged to remove mushroom pellets at 10,000× g for 20 min at 4° C. The supernatant was then adjusted to pH 4.0 and centrifuged at 12,000× g for 20 min at 4° C. to remove the protein fraction. The supernatant was then extracted with ethyl ether (first time: 200 mL, second and third times: 150 mL). The three ether fractions were combined, dried over anhydrous sodium sulfate and concentrated by rotary evaporation. This sample preparation was repeated five times to produce enough ODA for further separation.

Silicic Acid Column Chromatography

Silicic acid, 100 mesh (Sigma Chemical Co., St. Louis, Mo.), was cleaned prior to use as described by Hirsch et al., (1958). A column (2.5×40 cm) containing 30 g washed silicic acid was used for the primary purification of the ethyl ether extract. The column was first eluted with 200 mL of 20% ethyl ether in pentane, followed by 200 mL of 50% ethyl ether in pentane. The eluate of 50% ethyl ether in pentane, containing the ODA, was concentrated by rotary evaporation for further purification.

Silica Gel Thin-Layer Chromatography

Concentrated eluates (20 µL) from column chromatography were applied to silica gel TLC plates (250 µm) containing a 254 nm fluorescent indicator (Sigma) and developed three times in a solvent system consisting of ethyl ether-heptane-glacial acetic acid (50:50:1, v/v). The separated spots were visualized under UV light, or located by spraying plates with 50% sulfuric acid and heating at 100° C. for 20 min (Mangold, (1961)). Acids on TLC plates were identified by spraying 0.05% bromophenol blue in 0.2% aqueous citric acid (Kennedy et al., (1951)). Aldehydes were detected on plates by spraying with a saturated solution of 2,4-dinitrophenol hydrazine in 2M HCl (Bush et al., (1962)).

The 50% ethyl ether in pentane eluate containing the ODA was purified by TLC on silica gel plates. After three developments, ODA was located by spraying a small strip at each side of the plate with a saturated solution of 2,4-dinitrophenyl hydrazine in 2M HCl and by UV light. The remaining ODA in the silica gel was scraped off from the plate, extracted with ethyl ether and then subjected to further characterization.

Characterization of 10-Oxo-trans-8-decenoic Acid

The ultraviolet (UV) spectrum of ODA in water was determined on a Gilford Model 250 spectrophotometer equipped with a 6051 recorder. The infrared (IR) spectrum of ODA in chloroform was recorded on a Perkin Elmer Model 281 spectrophotometer. Mass spectra of ODA were analyzed by electron-impact ionization (EI) at 70 eV and by chemical ionization (CI) using isobutane as reagent gas on Kratos MS 9/50 and Kratos MS 25 mass spectrometers, respectively. Nuclear magnetic resonance (NMR) spectra of ODA were obtained in $CDCl_3$ (deuterochloroform) using a Bruker WM 360 spectrometer resonating at 360.13 MHz for $^1H$ and 90.56 MHz for $^{13}C$. The $^{13}C$. spectrum was obtained with WALTZ decoupling.

Quantification of 10-Oxo-trans-8-decenoic Acid

ODA as purified herein was found to contain less than 5% of impurities by MS and NMR. The purity of ODA was then determined by titration with ethanolic NaOH. The molarity of NaOH was standardized by anhydrous oxalic acid which was dried overnight at 100° C. Three points in the titration curve, with the ratios of [A-] to [HA] equal to 1/3, 1/1 and 3/1, respectively, were chosen for the calculation of the dissociation constant (Ka) of ODA based on the Henderson-Hasselbalch equation (Mathews et al., (1990)):

$$pH = pKa + \log([A^-]/[HA])$$

For the TBA test, a modified method of Dahle et al., (1962) was applied. TBA reagent was made by dissolving 0.025M 2-thiobarbituric acid in 1M phosphoric acid. One/mL of ODA with various concentrations, 1 mL of 20% trichloroacetic acid and 2 mL of TBA reagent were added into a test tube with a screw cap. The mixture was heated in a boiling water bath for 15 min. After the tubes were cooled, the absorption of the mixture was measured at 455 nm, the absorption maximum in the spectra of the reacted mixture of 0.1 mM ODA and TBA determined on a Gilford Model 250 spectrophotometer. The standard curve for ODA using the TBA test was determined on a Bausch and Lomb Spectronic 20 spectrophotometer at 455 nm.

RESULTS

Figure 2:
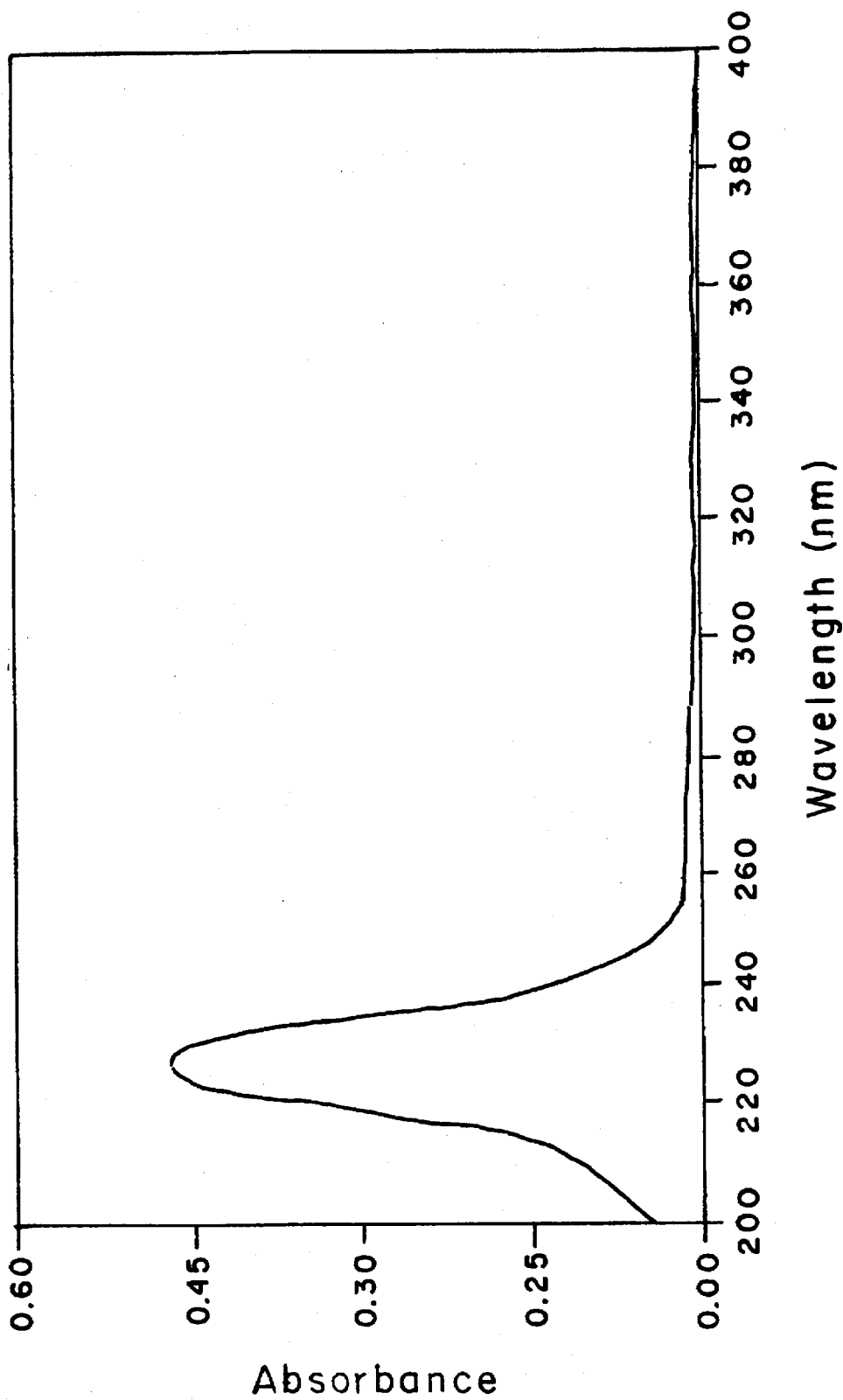
FIG. 2. Ultraviolet spectrum of 10-oxo-trans-8-decenoic acid in water.

The purified compound absorbed strongly in the UV region at 227 nm in water (FIG. 2), characteristic of an oxo-ene structure (Pomeranz et al., (1971)). Wurzenberger et al., (1982) found that the methyl ester of ODA had a strong absorption at 215 nm. This difference may be due to a shift of UV absorption after methylation. This compound was characterized as a UV-active compound ($\lambda max$ =227 nm) containing a double bond in conjugation with a carbonyl group.

Figure 3:
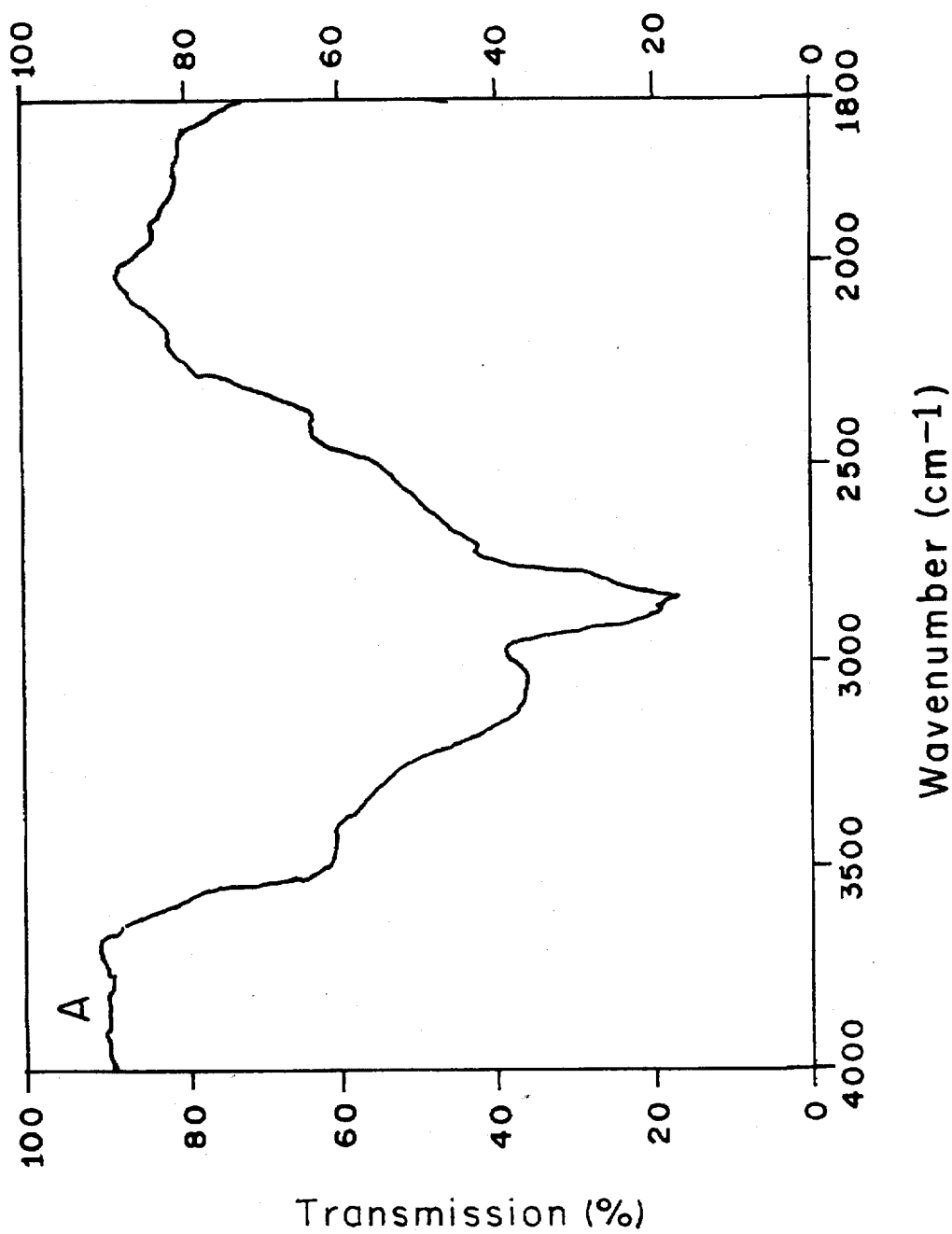
FIG. 3. Infrared spectrum of 10-oxo-trans-8-decenoic acid in chloroform (4000–1800 $cm^{-1}$).

The IR spectrum of the purified compound (FIGS. 3A and 3B) showed strong absorbances at 2815 and 1685 $cm^{-1}$ (aldehyde, —CH=O), 3040–3100 and 1705 $cm^{-1}$ (acid, —COOH), and 1635 $cm^{-1}$ (double bond, —CH=CH—) (Weast et al., (1983)). Furthermore, the 950 $cm^{-1}$ absorption indicated the presence of a trans double bond (Weast et al., 1983). The compound was further characterized to be one containing an aldehyde, a carboxyl group and a trans double bond.

Figure 4:
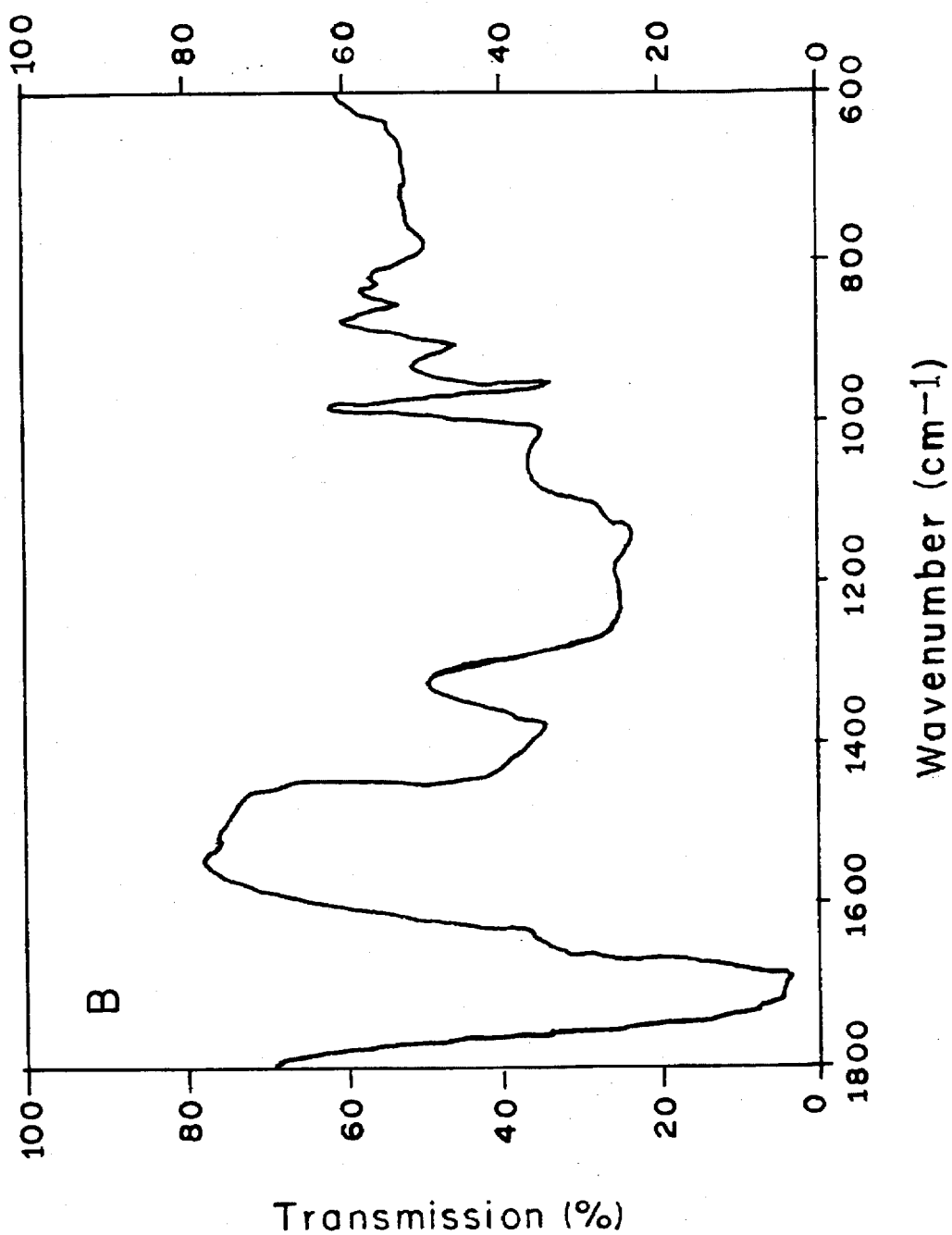
FIG. 4. Infrared spectrum of 10-oxo-trans-8-decenoic acid in chloroform (1800–600 $cm^{-1}$).
Figure 6:
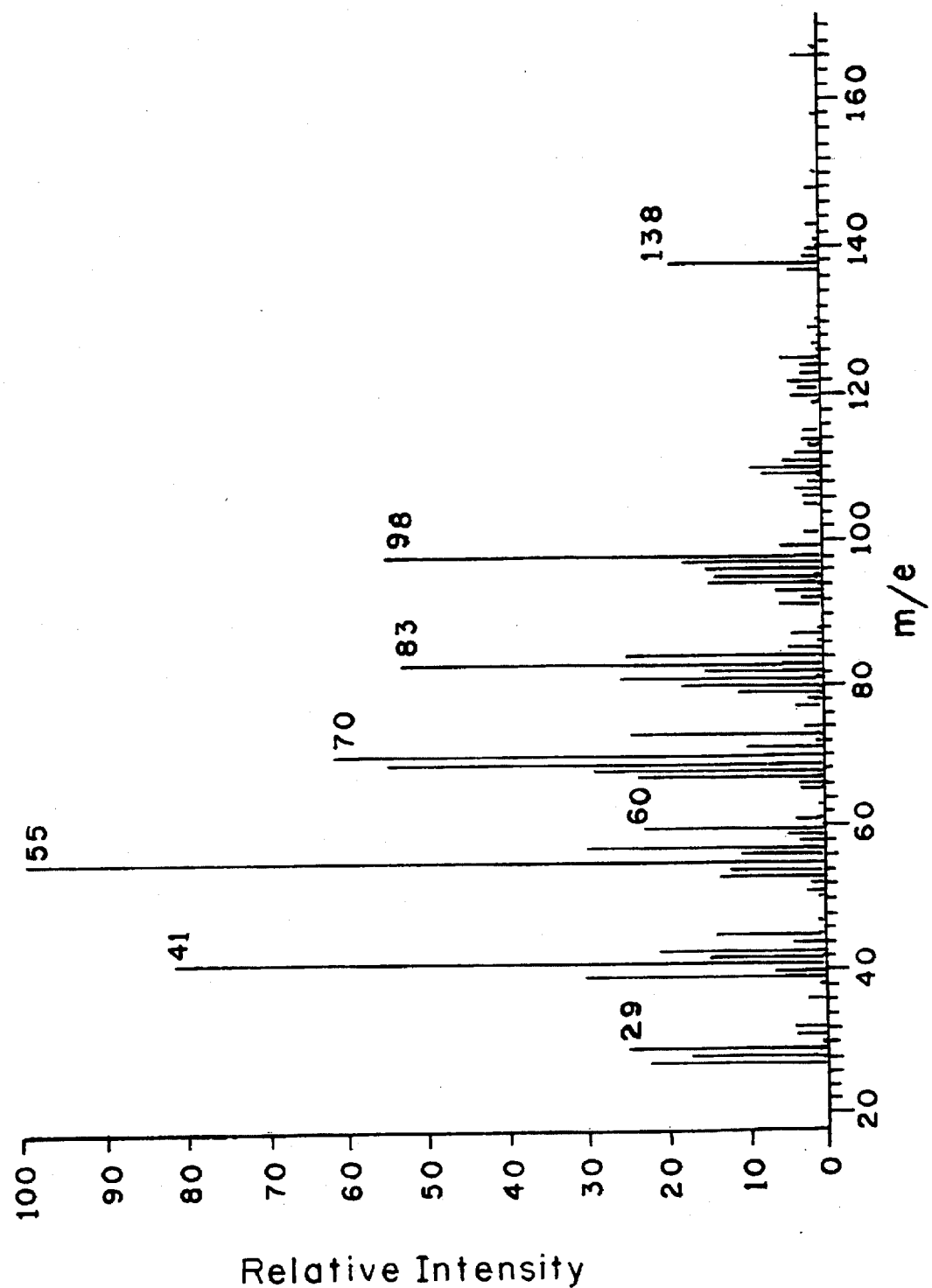
FIG. 6. Mass spectrum of 10-oxo-trans-8-decenoic acid by electron-impact ionization.

The mass spectrum of the purified compound obtained by chemical ionization (FIG. 4) showed that the M+1 ion was m/e 185, indicating a molecular weight of 184. In FIG. 4, the fragment ion, m/e 167, is a strong base peak and seemed more stable than the M+1 ion after chemical ionization. It was possibly formed from the M+1 ion by elimination of a water molecule (M-18). It has been reported that the fragment ion m/e 167 is formed from the M+1 ion m/e 199 of the methyl ester of ODA by elimination of a methanol molecule (M-32), but that the M+1 ion m/e 199 was more stable (Wurzenberger et al., (1982)). The fragment ion m/e 139 can also be formed by direct elimination of a formic acid (M-46) as illustrated in FIG. 6A. The CI mass spectrum (FIG. 4) indicated that the compound had a molecular weight of 184 and is a carboxylic acid.

Figure 5:
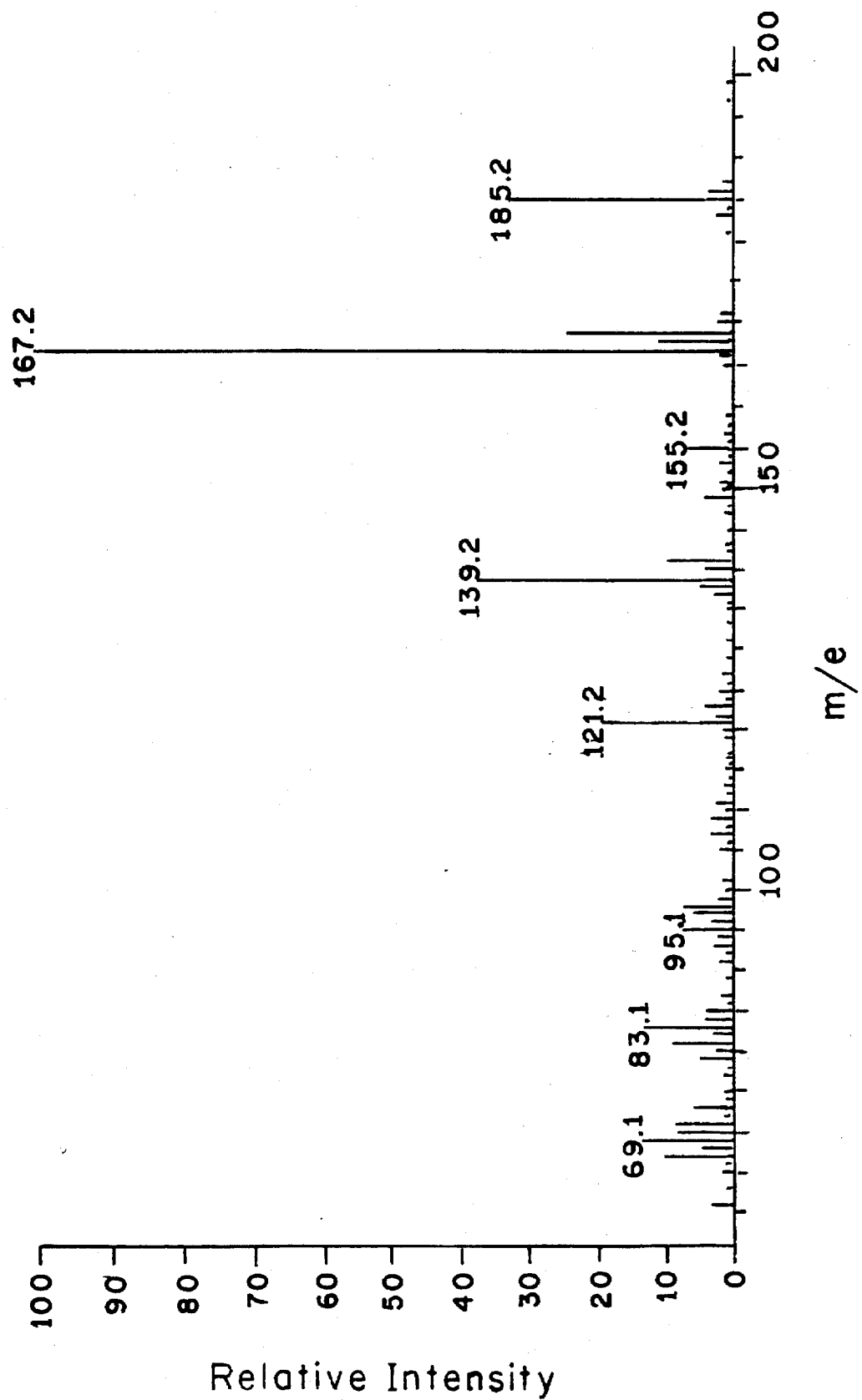
FIG. 5. Mass spectrum of 10-oxo-trans-8-decenoic acid by chemical ionization.

The EI mass spectrum of the purified compound is presented in FIG. 5. No molecular ion (M) was formed and the fragment ion m/e 55 was the major fragment ion (the base peak) after electron ionization, indicating that the compound fragments easily, and probably has a fragment group (O=CH—CH=CH+). The major fragmentions of the compound are m/e 41, 55, 69, 70, 83, 98, 138 and 166. The theoretical fragmentation is illustrated in FIG. 6B. The fragment ion m/e 41 appears to be the fragment of the compound produced by cleavage at the double bond, and probably has the structure O=C=CH+. Fragment ions m/e 69, 70, 83 and 98 seem to be the fragments of the compound produced by cleavage at carbons away from the double bond. Obviously, the CI and EI mass spectra are different from each other. Two small fragment ions (m/e 138 and 166) found in the EI mass spectrum are similar to those (m/e 139 and 167) in the CI mass spectrum and may be produced by elimination of a water and a formic acid, respectively.

The EI mass spectrum of the compound was similar to that of the methyl ester of ODA (Wurzenberger et al., (1983); Tressl et al., (1982)), and was consistent with that of the homologoue, the methyl ester of 12-oxo-trans-10-dodecenoic acid (Noble et al., (1971); rick et al., (1976); Zimmerman et al., (1979)).

Figure 7A:
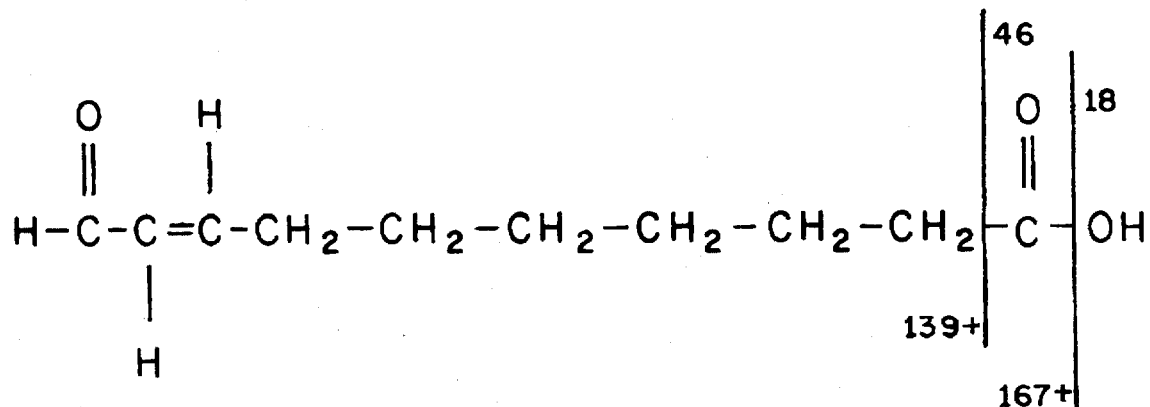
FIG. 7. Theoretical fragmentation of 10-oxo-trans-8-decenoic acid by (A) chemical ionization and (B) electron-impact ionization.
Figure 7B:
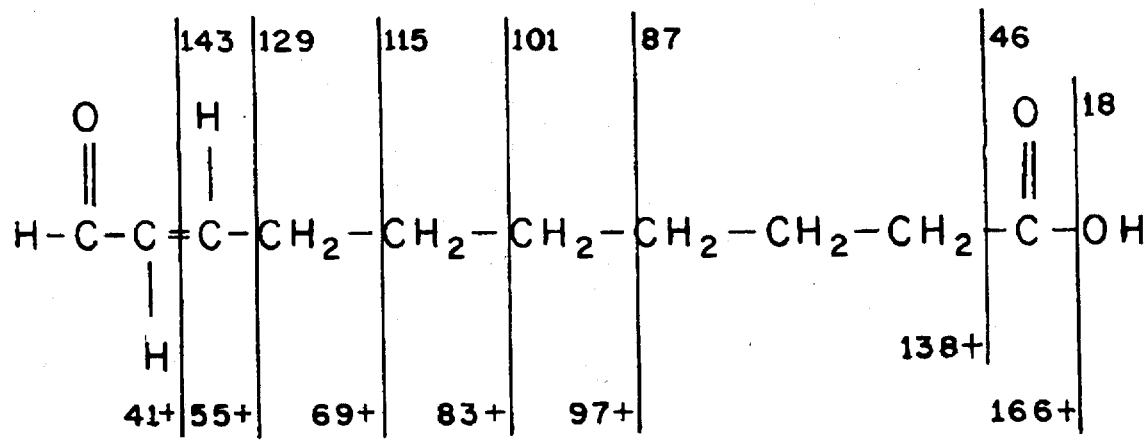
Figure 8:
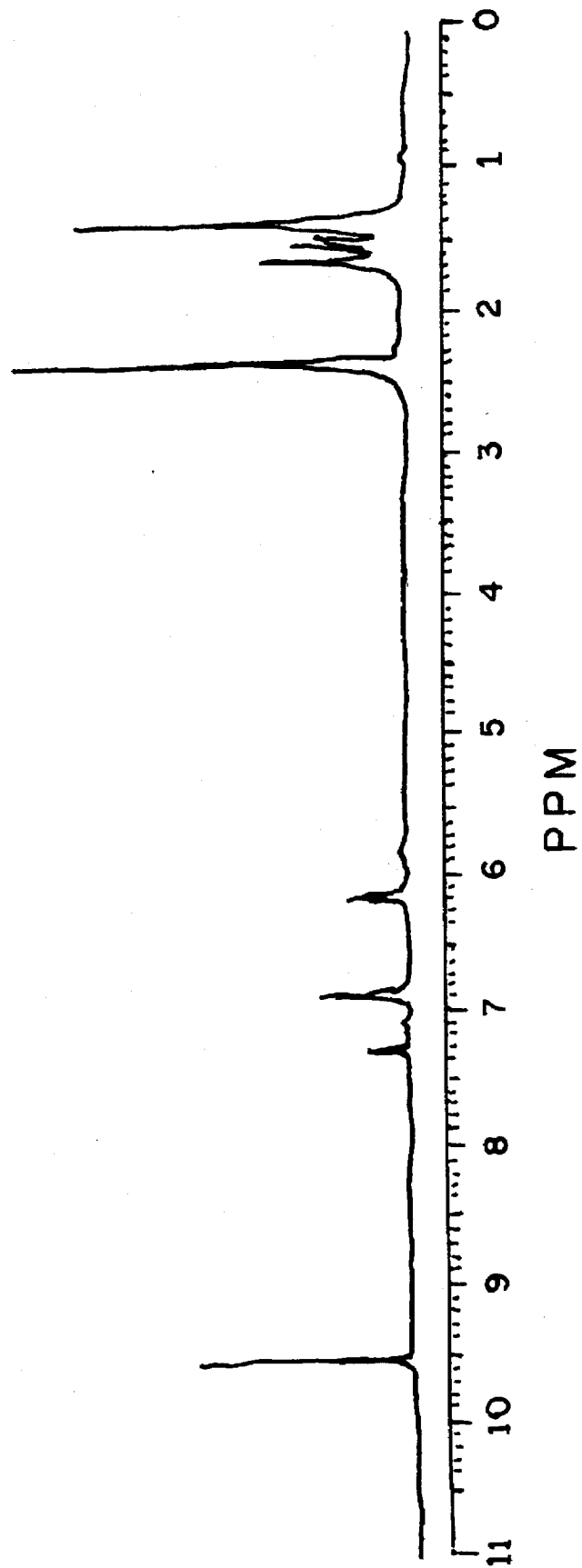
FIG. 8. $^1$H-Nuclear magnetic resonance spectrum of 10-oxo-trans-8-decenoic acid in $CDCl_3$.
Figure 11:
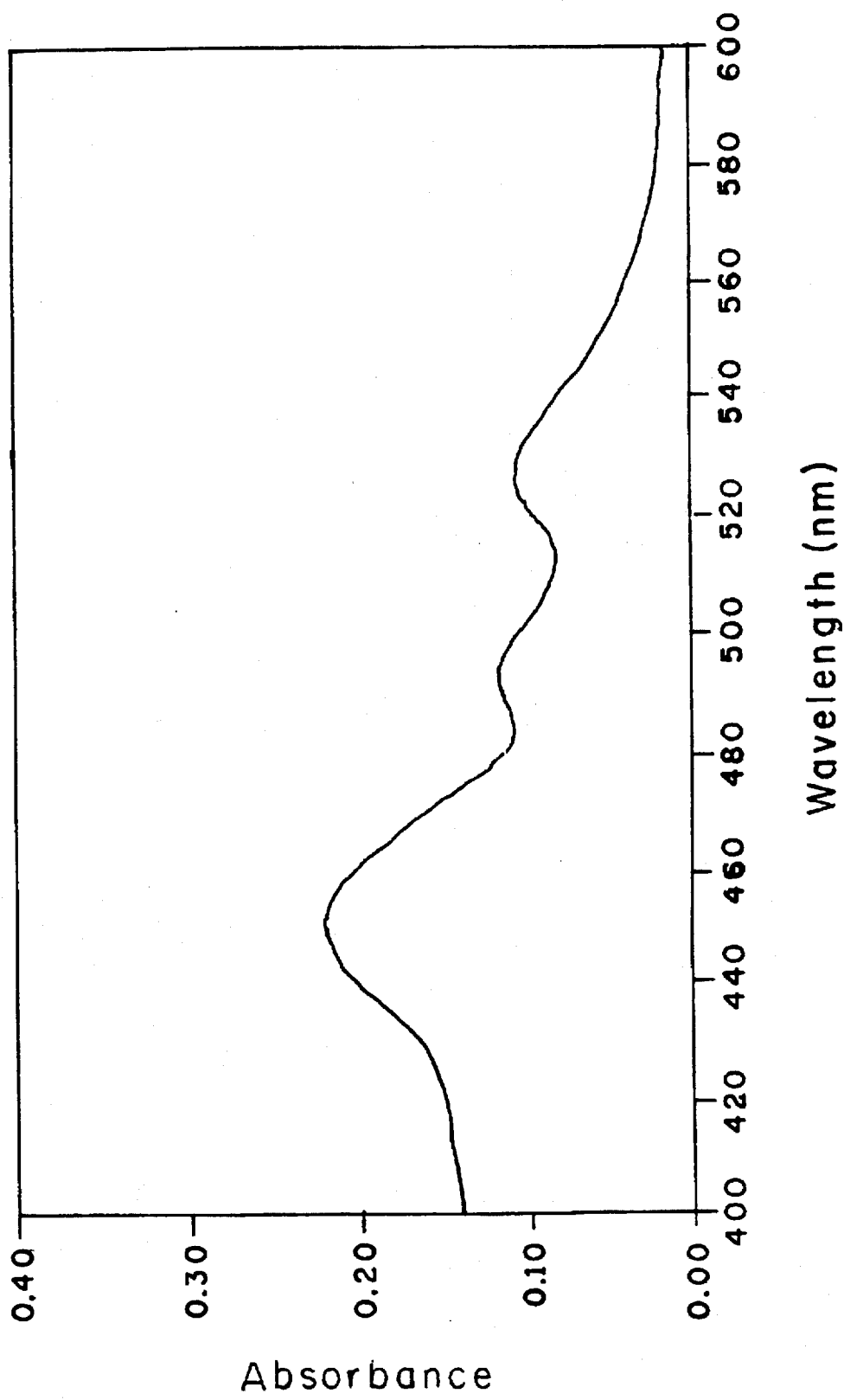
FIG. 11. Absorption spectrum of 10-oxo-trans-8-decenoic acid reacted with 2-thiobarbituric acid at 100° C. for 15 min.

The $^1$H NMR spectrum (FIG. 7) indicated that the compound had an aldehyde ($\delta$9.50) and a double bond ($\delta$6.85 and 6.15) (Mohacsi, (1964)). The $^{13}$C NMR spectrum (FIG. S) showed eight separate peaks and one overlapping peak, indicating 10 carbons in the compound. The spectrum also indicated that this compound had an aldehyde ($\delta$194), a carboxyl group ($\delta$180), and a double bond ($\delta$159 and 133) which is in conjugation with the aldehyde (Dyer, 1965; Bus et al., (1977); Gunstone et al., (1977)). After integration of $^1$H NMR spectrum, the resonated compound was measured to contain only 15 bound hydrogen atoms. The hydrogen atom at the carboxyl group of ODA was not always detected due to free dissociation after resonance. Therefore, 16 hydrogen atoms were confirmed in the compound. Three oxygens were needed for an aldehyde and a carboxylic acid. Finally, the compound was characterized to have a formula of $C_{10}H_{16}O_3$.

To determine the characteristics of the double bond, the hydrogen at position C9 was selectively irradiated at low power, and the irradiated $^1$H NMR spectrum was recorded. If the double bond was a cis structure, a magnetic signal transfer from the hydrogen nucleus of C9 to the adjacent hydrogen nucleus of C8 could be expected (Benesi, (1991)). From the result shown in FIG. 9, no net magnetic signal transfer was determined. This indicated that these two hydrogen nuclei were not close to each other. In fact, they were on opposite sides of the double bond. In other words, the double bond of the compound is in a trans configuration.

In conclusion, the purified compound was characterized as 10-oxo-trans-8-decenoic acid (O=CH—CH=CH—CH$_2$—CH$_2$—CH$_2$—CH$_2$—COOH, $C_{10}H_{16}O_3$) with a molecular weight of 184.

Properties of 10-Oxo-trans-8-decenoic Acid

During the characterization of the compound, mass and NMR spectra also showed that the purified compound contained more than 95% of ODA. The purity of ODA in the compound was further determined by titration to be 97.5 ±0.5%. In aqueous solution, the dissociation constant (Ka) of ODA was measured to be $10^{-4.68}$ with a standard deviation of $10^{0.04}$ using the Henderson-Hasselbalch equation (Mathews et al., 1990). ODA was a white, waxy solid soluble in acetone, chloroform, ethanol, ethyl ether, methanol, methylene chloride and water, and slightly soluble in non-polar solvents such as pentane, hexane, heptane and benzene.

A widely used test for lipid oxidation is the measurement of the red 532-nm-absorbing pigment produced upon reaction with 2-thiobarbituric acid (TBA) (Dahle et al., (1962)). Aldehydes other than malonaldehyde, such as alk-2-enals, can react with TBA to form yellow, orange, and red pigments (Kosugi et al., (1987)). Because ODA is a product of lipid oxidation, and also has the structure of a 2-ene-aldehyde similar to alk-2-enals, the reaction of ODA with TBA could be expected. The absorption spectrum showed that ODA could react with TBA to form a yellow 455 nm-, orange 495 nm-, and red 532 nm-absorbing pigment (FIG. 10). By measuring the absorbance at 455 nm, a standard curve for the quantification of ODA by the TBA test to a concentration of 0.2 mM could be obtained. However, the application of the TBA test to quantify ODA in mushroom homogenates is limited by the interference of other aldehydes concurrently formed from lipid oxidation and the dark color of mushroom homogenate.

A yield of about 10% of the ODA formed from linoleic acid with a purity of 97.5% was obtained. The low recovery is due to the low efficacy of batch type extraction. Continuous liquid-liquid extraction could potentially increase the yield. The two centrifugations could be combined into one by adjusting the pH after homogenization. Silicic acid chromatography was an efficient method of purification with high recovery.

To the inventors' knowledge, this is the first time ODA has been purified as the free acid, instead of its corresponding methyl ester (Tressl et al., (1982); Wurzenberger et al., (1982)). The purified ODA is suitable for use in mushroom production to study its effects on the mycelium growth, fruiting initiation and production yield.

EXAMPLE 2

Effect of 10-Oxo-trans-8-decenoic Acid on the Growth of Agaricus bisporus

Mushroom mycelium

The commercial mushroom spawn (hybrid off-white), *Agaricus bisporus* (Lange) Imbach, was obtained from Alpha Spawn Co., Avondale, Pa., and inoculated onto potato dextrose yeast (PDY) agar (Difco) and incubated at 25° C. A pure culture was obtained from the grain spawn grown on petri dishes and re-inoculated into PDY agar and maintained at 25° C. before use.

Medium preparation and culture incubation

The mushroom culture was grown on PDY agar or in PDY broth, both containing 0.5% yeast extract. The broth was dispensed into flasks prior to autoclaving, 50 mL. per flask, while 5 mL of sterile ODA solutions were aseptically added into flasks before inoculation.

To prepare ODA solutions, about 18.4 mg (0.1 mmole) of 10-oxo-trans-8-decenoic acid prepared as described above were dissolved in i mL ethanol and diluted with deionized water to 100 mL to give a molar concentration of $10^{-3}$M, and then diluted in order to add 1.0 mL of the solutions to each flask to give the required final concentrations.

Sterile ODA solutions were aseptically added into the autoclaved agar medium to achieve the desired final ODA concentrations, and then the medium was dispensed into petri dishes, ca 30 ml per dish. The levels of ODA tested included $2\times10^{-4}$, $10^{-4}$, $10^{-5}$, $10^{-6}$ and $10^{-7}$M for both PDY agar and broth. These flasks and dishes were inoculated with 1 mm mycelial plugs from 4-week old cultures and incubated statically at 25° C. for 5 weeks. Each week, ca 300 µL of broth was aseptically taken from the flasks for laccase assay, while the colony diameter of every petri dish was measured using a vernier caliper to calculate the linear growth of the culture.

Laccase assay

The activity of laccase was assayed as described in Leonowicz et al., (1981). The reaction mixture consisted of 1.0 ml of 0.04M MES (2-[N-morpholino] ethanesulfonic acid, Sigma)-NaOH buffer, pH 5.3, 200 µL of 0.5 mM syringaldazine (4-hydroxy-3,5-dimethoxybenzaldehyde, Sigma) in EtOH, and 100 µL of culture broth withdrawn from the flasks making up a final volume of 1.3 mL. The control mixture contained no culture broth. The change in absorbance was monitored for 5 mins at 525 nm. Laccase activity was expressed in units of kat, the conversion of 1 mole of syringaldazine per sec.

Dry matter determination

After 5-weeks of incubation, the dry matter of mycelia was determined by vacuum filtering liquid cultures in PDY broth through weighed filter paper, and drying to constant weight at 70° C.

Mushroom stipe preparation

Mushrooms, *Agaricus bisporus* (off-white and hybrid off-white), were grown on traditional horse manure-based compost at the Mushroom Test and Demonstration Facility (MTDF) and Mushroom Research Center (MRC) on the Pennsylvania State University campus using standard cropping procedures. Four type strains of mushrooms were used: the white, off-white, hybrid white (U3) and hybrid off-white (U1). Mushrooms from each flush were harvested before the veil was broken. Freshly harvested mushrooms were transported within about one hour after harvest to Borland Laboratory and placed in the pilot plant cold room (4° C.) for about two hours before sampling. Mushrooms were sorted on the basis of size and appearance. Diseased, damaged, misshapen, veil-opened and extremely large or small mushrooms (>40 or <25 mm in cap diameter) were discarded. Mushrooms of uniform size (25–40 mm) and maturity of the button stage (stage 1, veil intact tightly) were used in this research.

Figure 12:
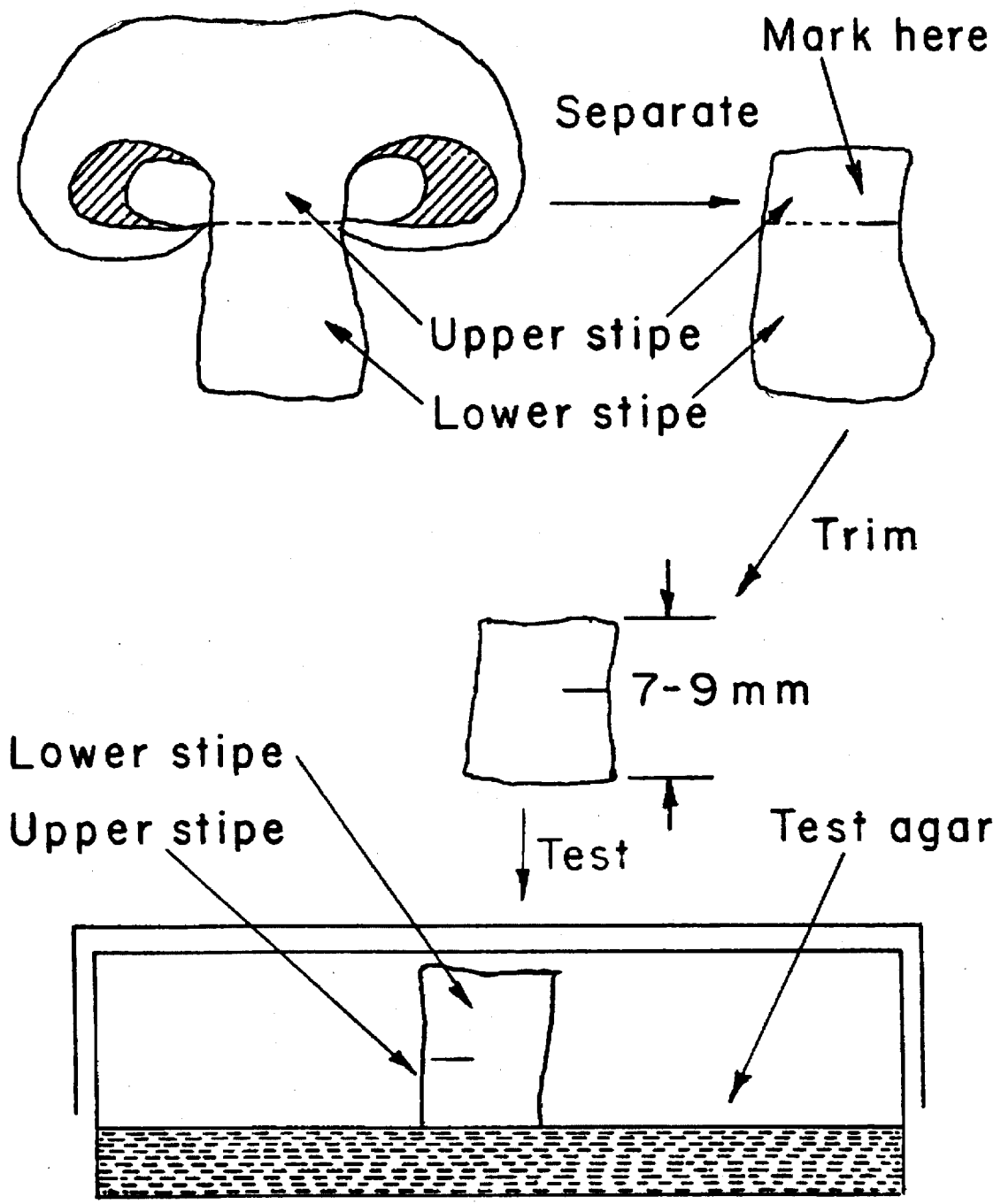
FIG. 12. Flow diagram for preparation and test of a separated mushroom stipe.

Mushrooms were dissected with a razor blade into whole stipes as shown in FIG. 12. Whole stipes were cut at the lower portions to a length of 7–9 mm to standardize the sample, and marked at the middle of the veil, which is the location where the veil attaches to the stipe, to indicate the upper and lower stipes. The separated stipes contained 2–4 mm of upper stipes and 5–6 nun of lower stipes. For the study using separated upper stipes, mushrooms were dissected directly into upper stipes with a length of 3–5 mm. The separated stipes or upper stipes were put upside down on the test agar containing various mushroom supernatants or ODA concentrations; i.e., the upper sides in contact with the agar surface (FIG. 12). All petri dishes were covered and stored at 12° C. The length of separated stipes and upper stipes was measured using a vernier caliper before and after certain days of storage.

Mushroom supernatant preparation

Three mushroom supernatants were made using the method similar to the procedure for 1-octen-3-ol analysis (Mau, (1992)). Mushroom supernatants were prepared by blending 50 g of mushrooms with 100 mL of 0.1M Na phosphate buffer, pH 6.5, and linoleic acid (0, 25.6 and 51.2 mg for supernatants A, B and C, respectively). 1-Nonanol was added as an internal standard prior to blending in order to quantify 1-octen-3-ol. After pentane extraction and centrifugation, the pentane layer was removed for 1-octen-3-ol assay, and the supernatant (ca 135 ml) was adjusted to the final volume of 200 mL using deionized $H_2O$. Due to the fact that 1-octen-3-ol and 10-oxo-trans-8-decenoic acid are formed at the molar ratio of 1:1 (Wurzenberger et al., (1982)), the concentrations of ODA in supernatants were computed directly from the 1-octen-3-ol content to be $2.7 \times 10^{-5}$, $4.8 \times 10^{-4}$, and $9.4 \times 10^{-4}$M for supernatants A, B and C, respectively.

Test agar preparation

The test agar (2%) was prepared by suspending 23 g of agar (Difco) in 1 L deionized $H_2O$, heating to boiling to dissolve completely, autoclaving for 15 min at 121° C., and cooling to 50°–55° C. prior to adding supernatants or ODA solutions. Sterile mushroom supernatants (25 mL), phosphate buffer and deionized $H_2O$ were added aseptically into 175 mL agar solution prior to dispensing into dishes. The agar solution was then dispensed into petri dishes, ca 16.7 mL per dish. The concentrations of ODA in the 2% agar were calculated to be $3.4 \times 10^{-6}$, $6.0 \times 10^{-5}$, and $1.2 \times 10^{-4}$M for treatments 3, 4 and 5. All agar contained 12.5 mM phosphate buffer except the control. Mushrooms (off-white) from the first, second and fourth flushes were used to study their postharvest growth after 6-day storage at 12° C.

Sterile ODA solutions were aseptically added into the autoclaved agar solutions to achieve the desired final ODA concentrations. The agar solution was then dispensed into dishes, ca 20.8 mL per dish. The level of ODA tested included $10^{-4}$, $10^{-5}$, $10^{-6}$, $10^{-7}$, and $10^{-8}$M. Mushrooms (hybrid off-white) from 6 different crops were used to study their postharvest growth. In the first 2 experiments, mushroom stipes were measured after 4-day storage at 12° C. In order to prevent stipe deterioration and desiccation of the test agar, in the following experiments mushroom stipes were measured after 3-day storage at 12° C.

Mushroom powder preparation

Mushroom powder A was prepared directly from freeze-dried whole mushrooms. Mushroom powder B was prepared from freeze-dried mushroom homogenate which was made by blending mushrooms with 0.1M Na phosphate buffer, pH6.5, at the ratio of 1:1 (v/w). Mushroom powder C was prepared from freeze-dried mushroom homogenate which was made by blending mushrooms with phosphate buffer and linoleic acid (0.5 mg/g mushroom). 1-Nonanol was added during the preparation of mushroom powders B and C. The concentration of ODA in the mushroom powders B and C. was computed from the 1-octen-3-ol content to be 0.66 and 2.78 mg per g mushroom powders B and C, respectively. Since mushroom powder A was prepared from whole mushrooms without blending, ODA and 1-octen-3-ol content were considered to be zero.

Mushroom cropping

A crop of mushrooms, *Agaricus bisporus* (hybrid off-white), was grown at the Mushroom Research Center using standard cropping procedures (Schisler, (1967)), except for treatments as follows: (1) control-no supplementation; (2) addition of mushroom powder A to the casing layer at casing; (3) addition of mushroom powder B to the casing layer at casing; (4) addition of mushroom powder C to the casing layer at casing; (5) spraying of mushroom powder B to the casing layer 24 hrs prior to pinning; (6) spraying of mushroom powder C to the casing layer 24 hrs prior to pinning. At the time of casing, the trays were cased with a 4.5- to 5-cm layer of peat moss containing 140 g of colonized compost per 6.4 kg moist peat per tray or CACing material. The amount of mushroom powder applied was 12.5 g per tray except for the control, and the concentrations of ODA applied were 1.2 mg per kg casing layer for treatments 3 and 5, and 5.3 mg per kg for treatments 4 and 6. The experiment was a completely randomized design with 6 treatments and 5 replicates (trays) for each treatment. Mushrooms were picked before the veil was broken, and the crop continued for a 4-flush pick period. The weight and number of mushrooms were recorded daily for each tray.

Statistical analysis

The experimental data were subjected to a single classification analysis of variance (AOV) for a completely randomized design (Steele et al., 1980). Fisher's protected least significant difference (LSD) was applied to separate the means. The level of significance used in this research was 0.05.

RESULTS

Effect on growth of mushroom mycelium

Methods for the estimation of total fungal growth include the measurement of dry matter, linear growth, carbon dioxide evolution, chitin, ATP as well as extracellular laccase activity (Cochrane, (1958); Wood, (1979)). In this research the linear growth rate was used to examine the growth of mushroom mycelia on agar plates, while the extracellular laccase activity and dry matter were determined to estimate the growth of mycelia in liquid cultures. Extracellular laccases (p-diphenol: oxygen oxidoreductase, EC 1.10.3.2) produced by various classes of fungi are reported to be involved in biotransformation of lignin and lignosulfonate (Anders et al., (1976)), as well as in the breakdown of cellulose by cellulase (Westermark et al., (1974a); Westermark et al., (1974b); Haars et al., (1980)). Although the role of laccase in growth and development of Agaricus bisporus is not well defined, it has been observed that laccase production correlated with mycelial biomass of this fungus (Wood, (1979); Matcham et al., (1985); Claydon et al., (1988)).

On potato dextrose yeast (PDY) agar plates, the linear growth rate of mycelia was slightly increased by ODA at the concentration of $10^{-5}$M (1.84 ppm), and greatly increased at concentrations of $2 \times 10^{-4}$ and $10^{-4}$M (36.8 and 18.4 ppm) (Table 1). After 5 weeks of growth in liquid culture, the dry matter of mycelia at ODA concentrations of $10^{-6}$ and $10^{-5}$M was ca 3-fold higher than mycelia grown on the control medium (Table 2). Both the laccase activity and dry matter indicated that the mycelial growth was stimulated by ODA at $10^{-6}$ and $10^{-5}$M (0.184 and 1.84 ppm).

TABLE 1

Effect of 10-oxo-trans-8-decenoic acid on the linear growth rate of Agaricus bisporus mycelia (hybrid off-white) on potato dextrose yeast agar at 25° C.

| ODA added to PDY agar | | Linear growth | Relative linear |
|---|---|---|---|
| (M) | (ppm) | rate (mm/wk) | growth rate |
| 0 (Control) | 0 | 5.66 | 1.00 d* |
| $2 \times 10^{-4}$ | 36.8 | 9.85 | 1.88 a |
| $10^{-4}$ | 18.4 | 8.42 | 1.50 b |
| $10^{-5}$ | 1.84 | 6.40 | 1.14 c |
| $10^{-6}$ | 0.184 | 6.17 | 1.10 cd |
| $10^{-7}$ | 0.0184 | 5.90 | 1.05 cd |

*Values with the same letter within the same column are not significantly different at the level of 0.05.

TABLE 2

Effect of 10-oxo-trans-8-decenoic acid on laccase activity and dry matter of Agaricus bisporus mycelia (hybrid off-white) grown in potato dextrose yeast broth at 25° C.

| ODA added to PDY broth | LOG [Laccase activity (mkat/ml)] | | | | | Dry matter (mg) |
|---|---|---|---|---|---|---|
| | Week 1 | Week 2 | Week 3 | Week 4 | Week 5 | Week 5 |
| 0 (Control) | 0.49 c* | 1.19 d | 1.97 d | 2.37 d | 2.74 bc | 15.6 b |
| $2 \times 10^{-4}$ M (36.8 ppm) | 0.25 c | 1.84 cd | 2.07 d | 2.15 d | 2.38 c | 16.7 b |
| $10^{-4}$ M (18.4 ppm) | 1.04 bc | 2.13 c | 2.29 d | 2.38 d | 2.64 bc | 23.2 b |
| $10^{-5}$ M (1.84 ppm) | 1.63 a | 2.62 a | 2.90 a | 3.20 a | 3.53 a | 48.5 a |
| $10^{-6}$ M (0.184 ppm) | 1.16 b | 2.34 b | 2.76 b | 3.07 b | 3.43 a | 44.1 a |
| $10^{-7}$ M (0.0184 ppm) | 0.73 bc | 2.15 bc | 2.57 c | 2.86 c | 3.08 b | 16.9 b |

*Values with the same letter within the same column are not significantly different at the level of 0.05.

Using the measurement of linear growth, dry matter and laccase activity, ODA was found to have a significant stimulatory effect on mushroom mycelial growth on PDY agar and in broth. The effective concentrations were much lower in liquid cultures than on agar plates. The slow diffusion of ODA to the mycelium grown on top of agar plates might be a limiting factor accounting for the differences in effective concentrations. 1-Octen-3-ol has been found in mushroom mycelia (Schindler, (1989); Grove, (1981)). Thus, by inference, it is apparent that ODA is also produced when the filaments of mycelia are damaged or disrupted. ODA produced in damaged filaments may migrate to adjacent filaments, and there, stimulate mycelial growth. Like traumatin in higher plants, ODA may stimulate mycelial growth in response to wounding.

Effect on postharvest growth of mushroom stipes

Due to its rapid elongation during postharvest storage, the mushroom stipe has been a subject of study since 1956 (Urayama, (1956)). Separated stipes, dissected from the mushrooms as shown in FIG. 12, were used to study elongation as influenced by crude preparations of ODA (mushroom supernatants) and purified ODA added to the test agar. Since the factor promoting stipe elongation was previously found to be mainly produced in the gills (Hagimoto et al., (1959); Hagimoto et al., (1960); Gruen, (1963); Gruen, (1967); Gruen, (1982)), upper stipes were placed in contact with test agar to simulate the normal growth condition. In this study, the elongation of stipes in excess of the control is referred as the additional elongation.

The effect of mushroom supernatants on the elongation of separated stipes is presented in Table 3. During storage (12° C.) in petri dishes with the test agar containing mushroom supernatants varying in their content of ODA, the upper portion of separated stipes lengthened more than the lower portion, even though the lower portion made up 65–70% of the original length before storage. Addition of crude preparations of ODA had a significant impact on the elongation of upper stipes, but no difference in the elongation of lower stipes was observed. The difference among the three supernatants (A, B and C) was the concentrations of linoleic acid prior to blending, i.e., the ODA concentrations after blending. These crude preparations of ODA significantly enhanced upper stipe elongation. However, compounds other than ODA might have been responsible for the stimulation of elongation above that of the control.

TABLE 3

Effect of mushroom supernatants on the elongation of separated stipes of Agaricus bisporus (off-white) after 6-day storage at 12° C.*

| Treatment† | ODA added‡ to test agar (M) | % Elongations§ | |
|---|---|---|---|
| | | Upper stipe | Lower stipe |
| 1 | — | 51.7 c | 33.0 a |
| 2 | — | 61.2 bc | 32.8 a |
| 3 | $3.4 \times 10^{-6}$ | 87.7 a | 28.9 a |
| 4 | $6.0 \times 10^{-5}$ | 81.7 a | 32.9 a |
| 5 | $1.2 \times 10^{-4}$ | 74.6 ab | 35.3 a |

*Separated stipes were put upside down on the test agar containing various mushroom supernatants; i.e., the upper stipes in contact with the agar.
†Treatment 1: 2% agar.
Treatment 2: Sodium phosphate buffer in 2% agar.
Treatment 3: Mushroom supernatant A in 2% agar.
Treatment 4: Mushroom supernatant B in 2% agar.
Treatment 5: Mushroom supernatant C in 2% agar.
‡Calculated from 1-octen-3-ol content on the basis of the molar ratio of 1:1.
§Values represent data averaged from the first, second and fourth flushes of the crop cycle. Values with the same letter within the same column are not significantly different at the level of 0.05.

ODA is formed as a result of mechanical damage of mushroom tissues, such as blending and cutting (Grosch et al., (1984); Schindler, (1989)). During preparation, mushroom stipes had been cut at both ends. ODA, or some other factor, released during cutting might have triggered the elongation of separated stipes (both upper and lower portions) in the control. In this study, it seems that the lower stipe responds only to the cutting since no differences were shown in the lower stipe elongation as a function of added ODA. This may be due to the limited diffusion of ODA from upper stipes to lower stipes.

Since the upper stipe was the major portion which responded to crude preparations of ODA, the following experiment used only upper stipes and applied pure ODA solns to the test agar. Because desiccation of the test agar sometimes occurred after 4 days of storage, in the third replication of this experiment and in subsequent experiments, the stipes were measured after 3 days of storage. The results showed no differences in the elongation of the upper stipes among treatments (Table 4), indicating that no additional elongation of upper stipes occurred other than that which occurred in response to the cutting during sample preparation.

TABLE 4

Effect of 10-oxo-trans-8-decenoic acid on the elongation of separated upper stipes of *Agaricus bisporus* (hybrid off-white) after storage at 12° C.*

| ODA added to test agar | | % Elongation of upper stipes† | | |
|---|---|---|---|---|
| (M) | (ppm) | 1 | 2 | 3 |
| 0 (Control) | 0 | 34.3 a | 33.3 a | 20.5 a |
| $10^{-4}$ | 18.4 | 34.8 a | 40.1 a | 17.7 a |
| $10^{-5}$ | 1.84 | 35.5 a | 36.5 a | 19.3 a |
| $10^{-6}$ | 0.184 | 39.9 a | 35.7 a | 16.6 a |
| $10^{-7}$ | 0.0184 | 41.0 a | 42.3 a | 18.1 a |
| $10^{-8}$ | 0.00184 | 30.1 a | 39.6 a | 15.8 a |

*Separated upper stipes were put upside down on the test agar containing various ODA concentrations; i.e., the upper sides in contact with the agar.
†Measured after 4-day storage for reps 1 and 2, and after 3-day storage for rep 3. Values with the same letter within the same column are not significantly different at the level of 0.05.

Because no differences were observed using upper stipes alone, separated stipes with both upper and lower portions were used to re-examine the effect of ODA. ODA had a significant effect on upper stipe elongation at all levels (Table 5). ODA stimulated the elongation of upper stipes in excess of the control, but the response occurred only when the lower portions were present. The additional elongation of upper stipes was stimulated by ODA at a concentration as low as $10^{-8}$M (0.00184 ppm).

TABLE 5

Effect of 10-oxo-trans-8-decenoic acid on the elongation of separated stipes of *Agaricus bisporus* (hybrid off-white) after 3-day storage at 12° C.*

| ODA added to test agar | | % Elongation of upper stipes† | | | |
|---|---|---|---|---|---|
| (M) | (ppm) | 1 | 2 | 3 | Mean |
| 0 (Control) | 0 | 14.5 b | 11.6 c | 17.1 c | 14.4 b |
| $10^{-4}$ | 18.4 | 25.1 a | 30.5 ab | 34.2 a | 30.0 a |
| $10^{-5}$ | 1.84 | 30.7 a | 25.0 b | 27.4 b | 27.7 a |
| $10^{-6}$ | 0.184 | 27.5 a | 24.7 b | 36.2 a | 29.5 a |

TABLE 5-continued

Effect of 10-oxo-trans-8-decenoic acid on the elongation of separated stipes of *Agaricus bisporus* (hybrid off-white) after 3-day storage at 12° C.*

| ODA added to test agar | | % Elongation of upper stipes† | | | |
|---|---|---|---|---|---|
| (M) | (ppm) | 1 | 2 | 3 | Mean |
| $10^{-7}$ | 0.0184 | 27.3 a | 38.3 a | 27.2 b | 30.9 a |
| $10^{-8}$ | 0.00184 | 23.7 a | 32.7 ab | 35.1 a | 30.5 a |

*Separated stipes were put upside down on the test agar containing various ODA concentrations; i.e., the upper stipes in contact with the agar.
†Values with the same letter within the same column are not significantly different at the level of 0.05.

The movement of dry matter from the stipe to the cap reportedly occurs even after harvest (Hammond et al., (1975); Murr et al., (1975)), and is apparently associated with mushroom development. The lower stipe has been found to be high in mannitol content (28% of dry wt) as compared to mannitol content in the gills (10%) and the upper stipe (19%) (Ajlouni, (1991)). Mannitol is considered to be the main respiratory substrate utilized by harvested mushrooms (Hammond et al., (1975)), and it can be translocated between the various tissues (Schmidt, (1977)). Also, translocation of mannitol and water from the lower to upper stipes can cause (or support) growth and cell enlargement of upper stipes (Ajlouni, (1991)). Therefore, with the lower stipe, the upper stipe could respond to the stimulatory effect of ODA. Without the lower stipe, the upper stipe elongation may be limited by mannitol availability. This is consistent with the finding that trimming the stipe of nameko (Pholiota nameko) (Minamide et al., (1985)) and *Agaricus bisporus* mushrooms (Ajlouni, (1991)) to 5 mm from the cap prevented the elongation of stipes and opening of caps, and improved shelf life of fresh mushrooms.

Comparing the results shown in Tables 3 and 5, it can be concluded that ODA is the factor contributing most to the additional elongation of upper stipes, and possibly the factor that triggers the initial stipe elongation after cutting, since it is produced when the tissues are damaged. During normal development of fruiting bodies ODA produced in the gills may translocate to the upper stipe and there stimulate stipe elongation. Therefore, ODA can be considered a hormone of mushroom fruiting bodies.

Effect on mushroom cropping

The effect of ODA on mushroom cropping was studied by supplementing mushroom powders containing various concentrations of ODA to the casing layer at casing or 24 hrs prior to pinning. In a mushroom cropping experiment at the Mushroom Research Center, the supplementation of mushroom powder A, prepared directly from freeze-dried whole mushrooms without blending and presumably containing no ODA, resulted in significantly lower mushroom yield and numbers as compared to the control (Table 6). Mushroom powders B and C supplemented at casing were more effective than those supplemented 24 hrs prior to pinning. Mushroom powders B and C supplemented at casing resulted in significantly higher mushroom yields and numbers at the first flush (break), while the average mushroom size was not affected by treatments (Table 6). However, no significant differences in mushroom yield or numbers were observed in the later flushes of the crop cycle. This may indicate that ODA was involved in the initiation of fruiting, but may be short-lived in its activity.

TABLE 6

Mean values of *Agaricus bisporus* (hybrid off-white) production parameters as influenced by mushroom powder supplementation to casing layer at casing or 24 hrs prior to pinning

| Treatment* | ODA† applied (mg/kg casing layer) | (Yield‡ (kg/m²)) 1st flush | Total§ | Size‡ (g/mushroom) 1st flush | Total | Quantity‡ (mushroom/m²) 1st flush | Total |
|---|---|---|---|---|---|---|---|
| 1 | — | 4.30 c | 11.85 ab | 25.1 a | 14.0 abc | 175 b | 854b |
| 2 | — | 4.65 bc | 10.37 c | 23.5 a | 14.5 ab | 212 b | 721c |
| 3 | 1.2 | 5.25 ab | 12.11 ab | 22.7 a | 13.7 bc | 236 ab | 887 ab |
| 4 | 5.3 | 5.50 a | 12.40 a | 18.9 a | 13.0 c | 295 a | 960 a |
| 5 | 1.2 | 4.38 c | 12.14 ab | 26.0 a | 15.5 a | 174 b | 788 bc |
| 6 | 5.3 | 4.33 c | 11.41 b | 25.3 a | 14.5 ab | 174 b | 787 bc |

*Treatment 1: Control.
Treatment 2: Mushroom powder A added at casing.
Treatment 3: Mushroom powder B added at casing.
Treatment 4: Mushroom powder C added at casing.
Treatment 5: Spraying of powder B 24 hrs prior to pinning.
Treatment 6: Spraying of powder C 24 hrs prior to pinning.
†Calculated from 1-octen-3-ol content on the basis of the molar ratio of 1:1.
‡Values with the same letter within the same column are not significantly different at the level of 0.05.
§Values represent data obtained from the four flushes of the crop cycle.

Since ODA stimulated mushroom mycelial growth and stipe elongation, it can be considered a mushroom hormone. 1-Octen-3-ol and ODA are products concurrently formed in mushroom species and other fungi by lipoxygenase and hydroperoxide lyase enzymes. 1-Octen-3-ol is responsible for the fresh aroma of mushrooms and other fungi, while ODA seems to be an effective growth hormone in mushrooms. The hormonal effect of ODA and closely related derivatives thereof on other fungi is also expected.

EXAMPLE 3

Derivatives of 10-oxo-trans-8-decenoic Acid

As noted earlier, many higher plant hormones have been found in mushrooms, including indole-3-acetic acid, various auxins, gibberellins, ethylene, cytokinins, and zeatins (Hammond et al., (1985)).

As is well known in the art, numerous derivatives of these compound exist which have been shown to affect plant growth and development (Ray et al., (1983); Galston et al., (1980)). By analogy, it is therefore reasonably expected that closely related derivatives of ODA will exhibit ODA-like effects on mushrooms and other fungi, and such derivatives are encompassed by the present invention. Thus, derivatives of ODA that exhibit at least one ODA effect, e.g., stimulation of mycelial growth, enhancement of mushroom fruiting and yield, elongation of upper stipes, etc., are within the scope of the present invention.

As non-limiting examples of modifications to the basic structure of ODA meant to be included as derivatives thereof, there can be mentioned substitution(s) of various hydrogen atoms with $C_1$–$C_5$ alkyl groups or hydroxyl groups; salts of ODA such as sodium, potassium, ammonium, calcium, etc.; anhydrides; esters such as the methyl, ethyl, and ascorbyl esters, or esters with other alcohols, diols, or polyols; and compounds such as trans-8-decenedioic acid, 10-hydroxy-trans-8-decenoic acid, 10-methoxy-trans-8-decenoic acid; etc.

In all the applications to mushrooms and other fungi described hereinbelow, ODA and derivatives thereof, either alone or in various combinations of two or more, can be employed.

The ODA of the present invention is preferably used in purified form wherein the ODA has been separated from other further contaminating substances such as fungal debris and toxic substances. The ODA is preferably at least 50% by weight pure, more preferably at least 80% pure, and most preferably at least 90% pure.

When the ODA is used an active ingredient in a composition for stimulating fungal growth, the composition will usually contain 0.1 to 99%, preferably 0.1 to 90%, and most preferably 50 to 80% by weight ODA, based on the total weight of the composition. If the composition is a liquid, the ODA may be dissolved in an organic solvent which is then added to water to form an aqueous solution.

Fungally acceptable carriers which may be utilized in the compositions of the present invention include water, non-toxic buffers such as phosphate buffer, etc., non-toxic inert materials, nutrient solutions, and other conventional agriculturally useful carriers well known in the art.

EXAMPLE 4

Mushrooms and Other Fungi

Similarly, as the plant hormones previously mentioned are well known to exert their effects on plants of many diverse genera and species, it is also reasonably expected that ODA and its similarly-acting derivatives will exert their effects on a broad array of mushrooms and other fungi, many of which are of significant economic importance.

Non-limiting examples of such mushroom genera include the following:

| | | |
|---|---|---|
| Agaricus | Flammulina | Melanoleuca |
| Agrocybe | Grifola | Morchella |
| Auricularia | Gymnopilus | Mycena |
| Boletus | Gyromitra | Pholiota |
| Calvatia | Kuegneromyces | Phylacteria |
| Cantharellus | Lactarius | Pleurotus |
| Clitocybe | Lentinula (Lentinus) | Stropharia |
| Coprinus | Lepiota | Tremella |
| Drosophila | Leucocoprinus | Tricholoma |
| Dryphila | Marasmius | Volvariella |

Non-limiting examples of other fungal genera, incuding fermentable fungi, include:

| Alternaria | Endothia | Neurospora |
| --- | --- | --- |
| Aspergillus | Fusarium | Penicillium |
| Blakeslea | Monascus | Rhizopus |
| Cephalosporium | Mucor | Trichoderma | as well as fungi listed in the *American Type Culture Collection Catalogue of Fungi/Yeasts* (1987), 17th Edition, pages 422–446.

Examples of other mushrooms and fungi encompassed herein are disclosed at columns 11–12 of U.S. Pat. No. 4,803,800.

EXAMPLE 5

Combination of ODA with Other Mushroom Yield/Fruiting Stimulants

ODA and its derivatives can be employed in combination with other growth- or yield-enhancing materials such as protein- and/or lipid-rich supplements to further improve mushroom production. Useful supplements for yield enhancement have been described by Carroll et al., (1976).

Examples of such delayed-release nutrients are Spawn Mate, a soy-based product, described in U.S. Pat. No. 3,947,969, and Fast Break, a corn-based nutrient additive.

When used in combination with such nutrients, ODA and its derivatives can be employed in amounts in the range from about 4.5 mg to about 1.1 g per kilogram of nutrient material, or 0.1–20 ppm in compost.

For the manufacture of spawn, ODA and derivatives thereof can be added to sterilized grain in an amount of from about 0.5 ppm to about 10 ppm, and to liquid cultures in an amount of from about $10^{-7}$M, equivalent to about 0.0184 ppm, to about $10^{-4}$M, equivalent to about 18.4 ppm, and more preferably in an amount of from about $10^{-6}$M, equivalent to about 0.184 ppm, to about $10^{-5}$M, equivalent to about 1.84 ppm.

ODA and its similarly acting derivatives can also be incorporated at the time of CACing or into CACing material, i.e., shredded full-grown spawn-run compost or other suitable inoculated material, added to casing soil at the time of casing. When employed in this manner, ODA and its derivatives can be added to the CACing material in an amount of from about 0.1 mg to about 20 mg per kilogram of CACing material.

When added to compost at the time of spawning, ODA and its similarly acting derivatives can be added in an amount of from about 0.1 to about 20 mg/kg compost. When added to the casing layer at the time of casing, ODA and its derivatives can be added to the casing layer in an amount of from about 1.2 mg/kg to ab out 5.3 mg/kg casing layer.

Finally, ODA and its derivatives can be incorporated in a delivery system, such as encapsulation in a manner similar to that described at columns 5–6 of U.S. Pat. No. 4,803,800. Non-limiting examples of suitable gels and other polymers useful as encapsulating materials include alginates, polygalacturonic acid, gelatin, a mixture of gelatin and sodium alginate, agar, celluloses, polyacrylamide, urethane, polyvinylpyrrolidone, etc., as summarized therein and as herein incorporated by reference in their entirety.

EXAMPLE 6

Use of ODA in Mushroom Production

For the purpose of enhanced commercial or home mushroom production, ODA and its derivatives can be employed in the process of mushroom cropping at the time of spawning, casing (CACing), and waterings. CACing has been described by Vedder (1989).

At spawning or casing, ODA and its derivatives can be added into the compost or the casing layer in the form of:

(1) the pure compound(s);
(2) an aqueous solution thereof;
(3) mushroom powder; or
(4) mushroom homogenate.

The pure compound(s) and aqueous solutions can be added in an amount of from about 0.1 to about 20 ppm into compost by mixing with spawn, yield-enhancing supplements such as Spawn Mate, or other supplements.

Mushroom homogenates can be prepared by blending or homogenizing whole mushrooms, cull mushrooms, lower stipes, or root portions containing mycelium in water or buffer such as 0.1M sodium phosphate buffer, pH 6.5, with or without linoleic acid or oil hydrolyzate. Such homogenates can be added into the compost or casing layer in an amount containing from about 0.1 to about 20 mg ODA/kg compost or casing layer.

Mushroom powder can be prepared from mushroom homogenates by drying methods such as freeze-drying, spray-drying, or oven-drying. Such powder can be added into the compost or casing layer in an amount containing from about 0.1 to about 20 mg ODA/kg compost or casing layer.

After casing or CACing, ODA and its derivatives can be incorporated into irrigation water for mushroom waterings, and can be applied in an amount of from about $10^{-7}$M to about $10^{-4}$M ODA at each watering.

EXAMPLE 7

Use of ODA in Fungal Fermentation Processes

ODA and its derivatives can be added to solid or liquid culture media for the purpose of stimulating mycelial growth in a manner similar to that described above in Example 2.

Cultures can be grown on, for example, agar, or in liquid media, such as various broths, etc., as described in the *American Type Culture Collection Catalogue of Fungi/Yeasts* (1987), 17th Edition, pages 412–421. Methods for fermenting fungi in order to obtain products such as foods and beverages, industrial chemicals, amino acids, and nucleotides, vitamins, enzymes, pharmaceuticals, pigments, etc. are old and well known in the art. The use of ODA and its similarly-acting derivatives to stimulate mycelial growth can be employed to increase the amount of extracellularly-produced metabolites or biomass from which products such as these can be obtained in a more rapid, efficient, and economical manner.

Mycelial growth on solid or in liquid media can be stimulated by contacting fungal mycelia during growth with ODA or derivatives thereof, alone or in combination. When solid media are employed, the concentration of ODA can preferably be in the range of from about $10^{-5}$M, equivalent to about 1.84 ppm, to about $10^{-3}$M, equivalent to about 184 ppm. More preferably, the ODA concentration can be in the range of from about 10–5M to about $2 \times 10^{-4}$M, equivalent to about 36.8 ppm. When liquid media are employed, the concentration of ODA can preferably be in the range of from about $10^{-7}$M, equivalent to about 0.0184 ppm, to about $10^{-4}$M, equivalent to about 18.4 ppm. More preferably, the ODA concentration can be in the range of from about $10^{-6}$M, equivalent to about 0.184 ppm, to about $10^{-5}$M. ODA and derivatives thereof, either alone or in combinations of two or more, can be employed in a similar manner.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for the use of 10-oxo-trans-8-decenoic acid as a fungal growth hormone to stimulate mycelial growth of cultivated mushrooms comprising;
   (a) selecting a species of cultivated mushroom;
   (b) selecting a solid or liquid growth medium suitable for growth of said mushroom;
   (c) adding 10-oxo-trans-8-decenoic acid to said growth medium to achieve a final concentration of 10-oxo-trans-8-decenoic acid in said medium of about $10^{-7}$M to about $10^{-4}$M;
   (d) inoculating said mushroom into said growth medium containing 10-oxo-trans-8-decenoic acid;
   (e) culturing said mushroom; and
   (f) harvesting the mycelium of cultivated mushroom.

2. A method for the hormonal stimulation of fruiting in cultivated mushrooms comprising:
   (a) mixing mushroom spawn with compost;
   (b) growing mushroom mycelia from said spawn;
   (c) casing said compost with a casing layer supplemented with 10-oxo-trans-8-decenoic acid to achieve a final concentration from about $10^{-7}$M to about $10^{-4}$M;
   (d) culturing the mushrooms;
   (e) harvesting said mushrooms.

3. A method according to claim 1, wherein the said liquid culture medium is potato-dextrose yeast extract.

4. A method according to claim 2 wherein said 10-oxo-trans-8-decenoic acid is added to said casing layer in aqueous solution after casing said compost.

* * * * *